United States Patent [19]

Rowsey et al.

[11] Patent Number: 5,755,785
[45] Date of Patent: *May 26, 1998

[54] SUTURELESS CORNEAL TRANSPLANTATION METHOD

[75] Inventors: J. James Rowsey, Tampa; Joseph Patrick Collins, St. Petersburg, both of Fla.

[73] Assignee: The University of South Florida, Tampa, Fla

[*] Notice: The term of this patent shall not extend beyond the expiration date of Pat. No. 5,584,881..

[21] Appl. No.: 329,720

[22] Filed: Oct. 26, 1994

Related U.S. Application Data

[63] Continuation-in-part of Ser. No. 289,670, Aug. 12, 1994, Pat. No. 5,584,881.

[51] Int. Cl.$^6$ .................................................. A61F 2/14
[52] U.S. Cl. .................................................. 623/5; 606/166
[58] Field of Search .................................. 606/166; 623/5

[56] References Cited

U.S. PATENT DOCUMENTS

| | | | |
|---|---|---|---|
| 3,454,966 | 7/1969 | Rosen | 3/13 |
| 3,945,054 | 3/1976 | Fedorov et al. | 3/13 |
| 4,127,903 | 12/1978 | Schachar | 3/13 |
| 4,190,050 | 2/1980 | Bailey | 128/305.1 |
| 4,236,519 | 12/1980 | La Russa et al. | 128/305 |
| 4,429,696 | 2/1984 | Hanna | 128/310 |
| 4,563,779 | 1/1986 | Kelman | 623/5 |
| 4,662,881 | 5/1987 | Nordan | 623/5 |
| 4,718,420 | 1/1988 | Lemp | 128/310 |
| 4,772,283 | 9/1988 | White | 623/5 |
| 4,810,082 | 3/1989 | Abel, Jr. | 351/160 |
| 4,824,066 | 4/1989 | Smith | 248/500 |
| 4,842,599 | 6/1989 | Bronstein | 623/5 |
| 5,030,230 | 7/1991 | White | 623/5 |
| 5,139,518 | 8/1992 | White | 623/5 |
| 5,334,213 | 8/1994 | Price | 606/166 |

*Primary Examiner*—Michael H. Thaler
*Attorney, Agent, or Firm*—Stein, Schifino & Van Der Wall

[57] ABSTRACT

A method of repairing a cornea of an eye. A donor material of living tissue in the shape of a partial sphere having an exterior Bowman's membrane of living tissue, is first die cut to define an outline configuration including a central extent and a plurality of tabs extending outwardly therefrom. The tabs are then shaved to remove substantially all of the donor material therefrom leaving substantially only the Bowman's membrane. The eye to be repaired is then punched to form a central aperture in the cornea having a size and shape essentially that of the central extent of the donor material. A plurality of pockets are incised from the central aperture into the cornea, the pockets being positioned and sized and shaped to receive the respective shaven tabs when the central extent is positioned within the central aperture. The central extent is then positioned within the central aperture and the shaven tabs are imbricated into the respective pockets

14 Claims, 11 Drawing Sheets

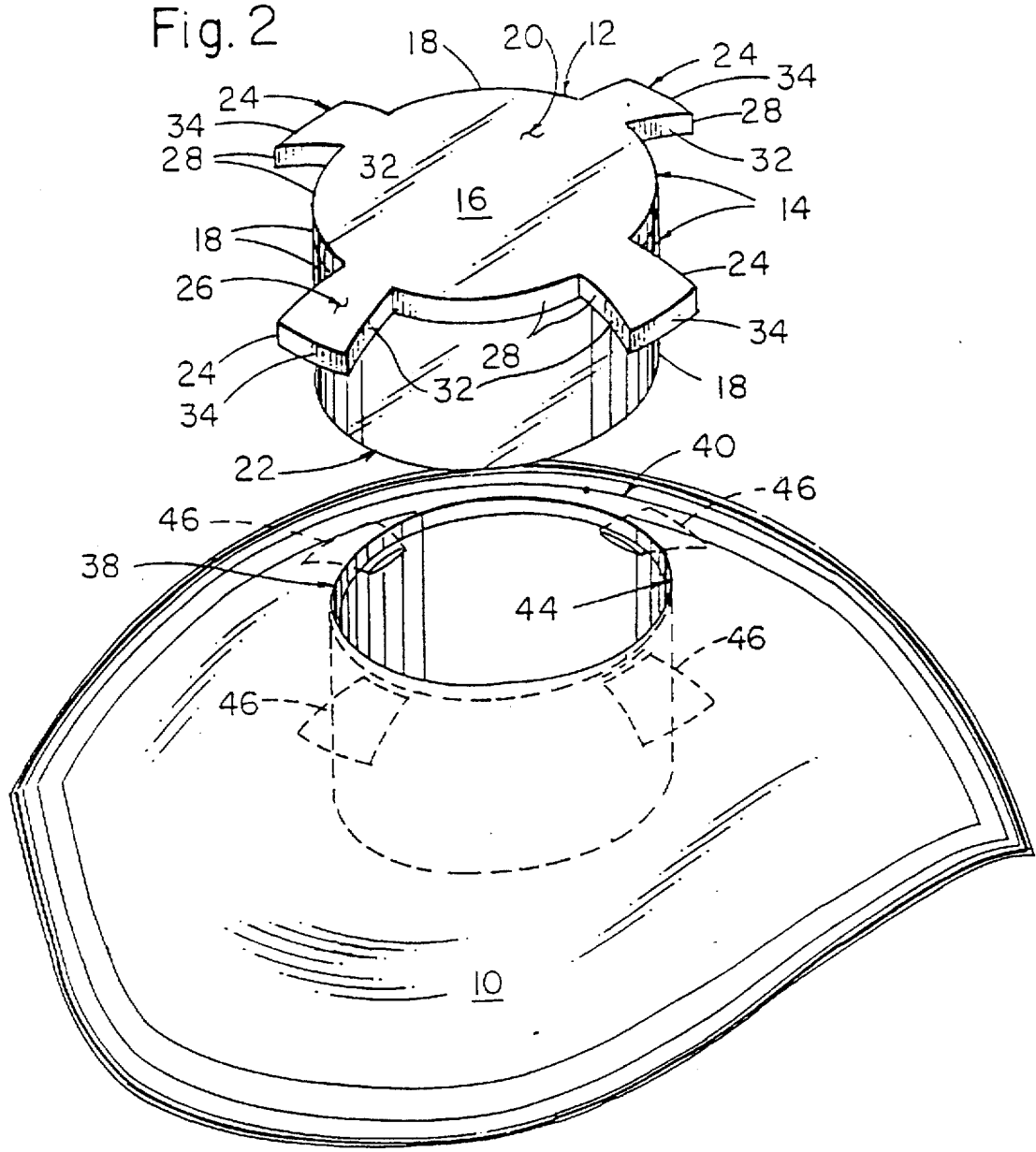

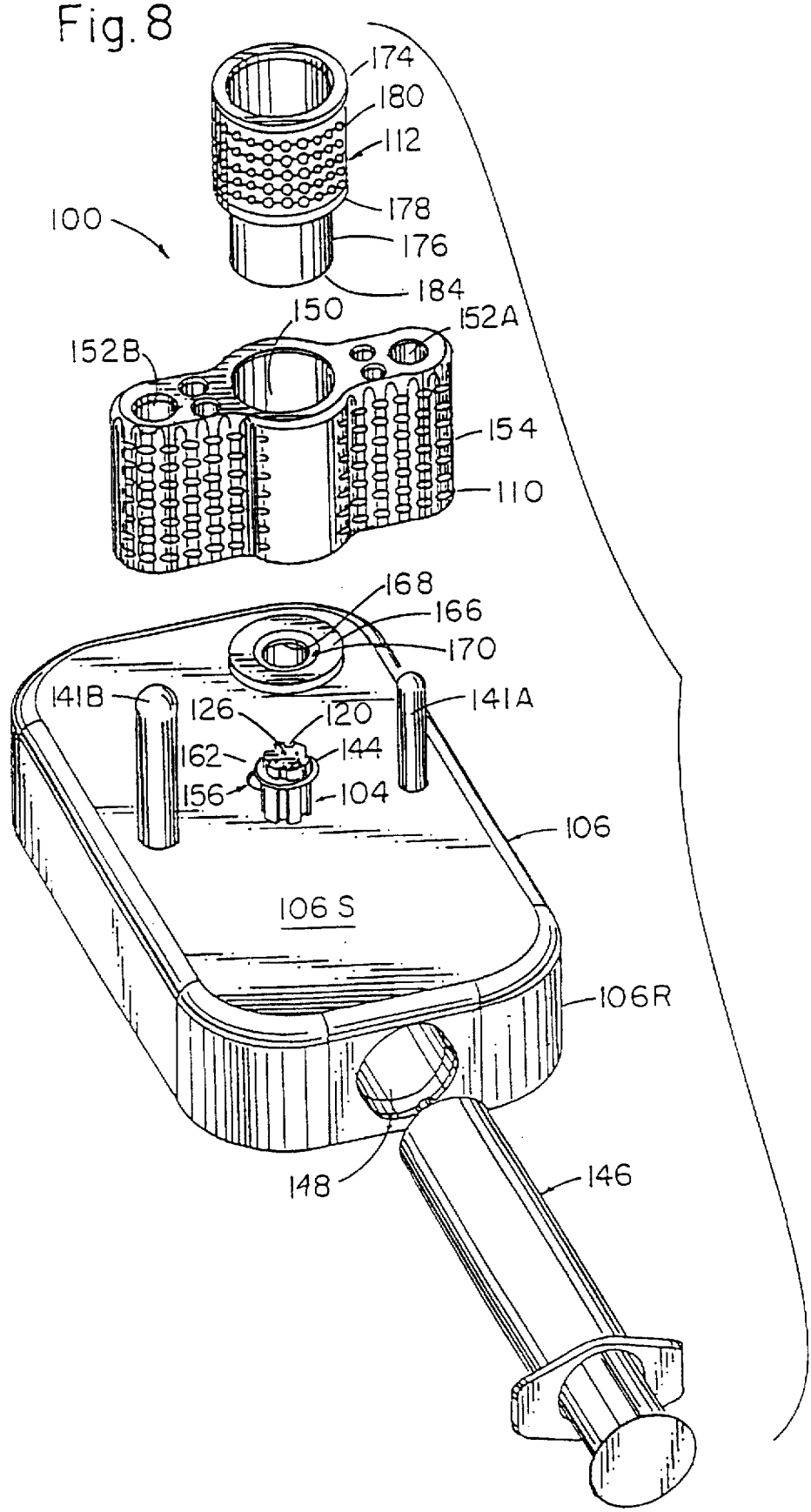

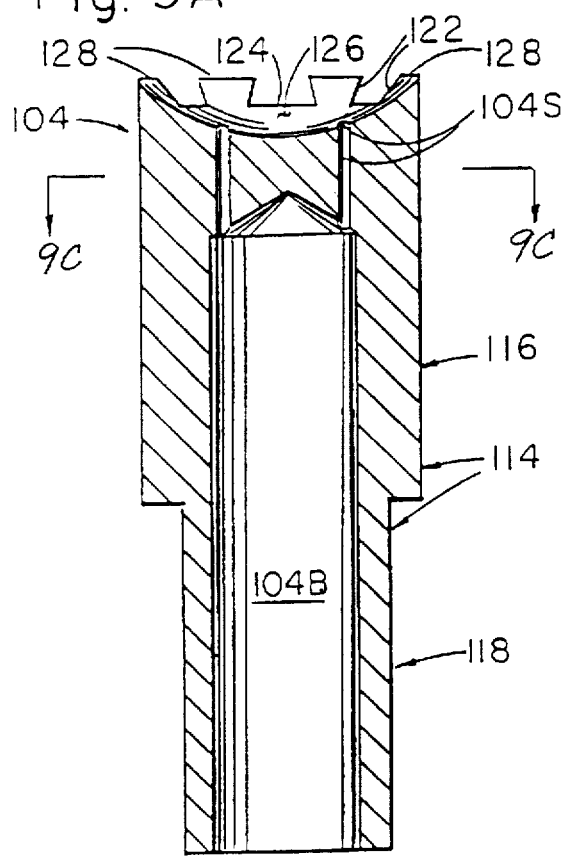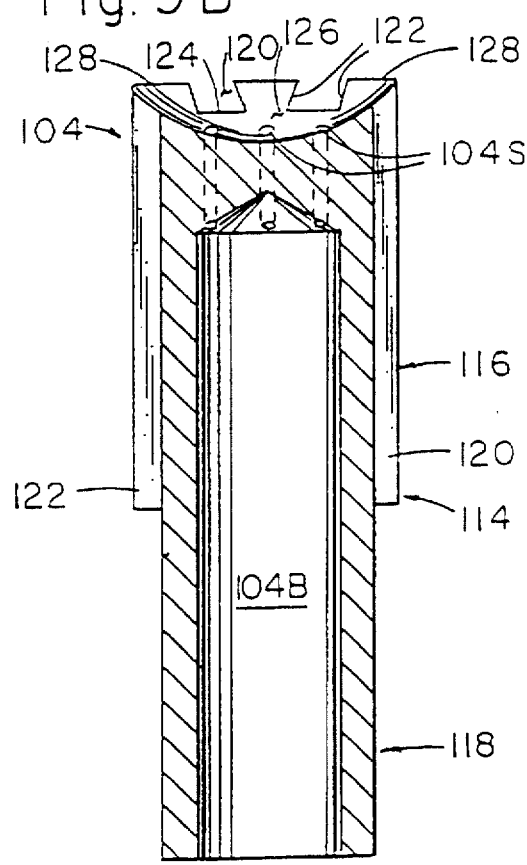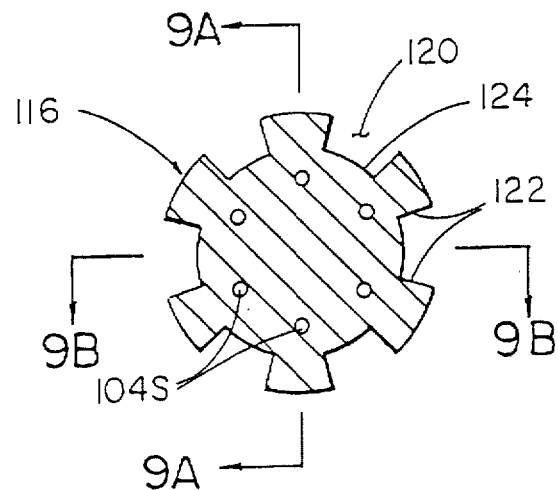

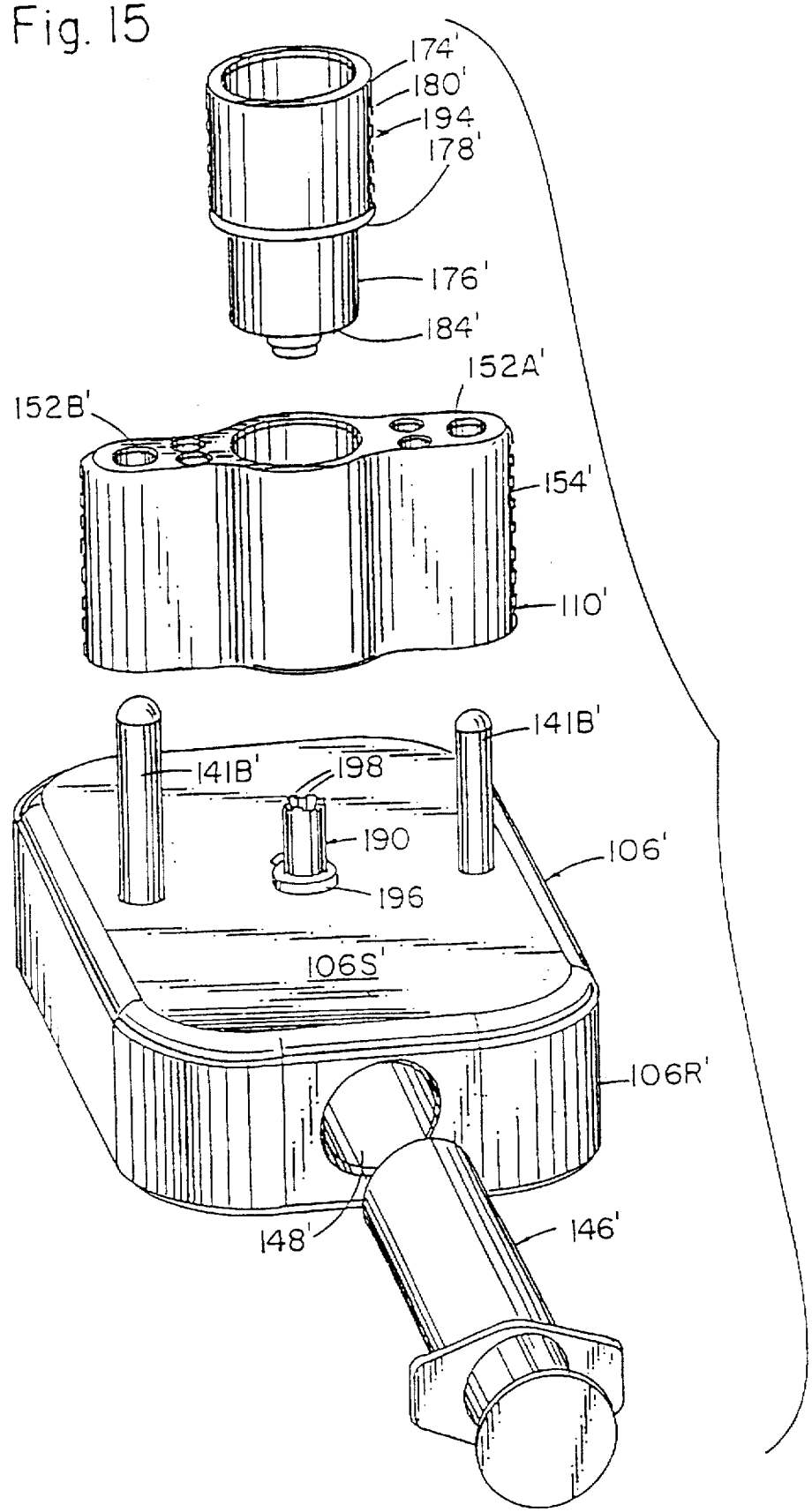

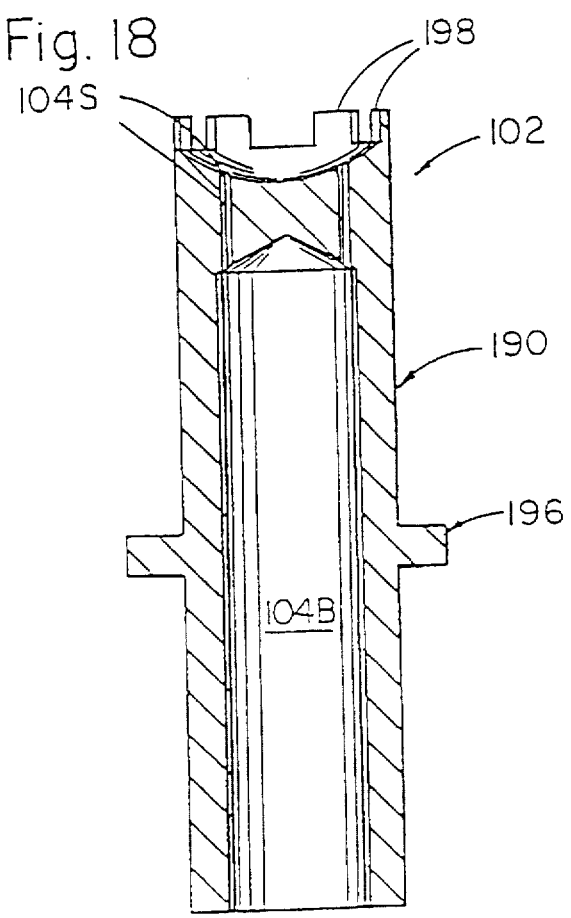

5,755,785

1

SUTURELESS CORNEAL TRANSPLANTATION METHOD

CROSS REFERENCE TO RELATED APPLICATIONS

This application is a continuation-in-part application of Ser. No. 08/289,670 filed Aug. 12, 1994 now Pat. No. 5,584,881

BACKGROUND OF THE INVENTION

1. Field of the Invention

This invention relates to sutureless corneal transplantation and, more particularly, to a method and apparatus for transplanting corneas with minimal or no sutures.

2. Description of the Background Art

Corneal transplantation occurs in approximately 37,000 patients in the United States per year. Each of these patients has delayed wound healing because of the avascular nature of the cornea. The stromal wound healing is facilitated by sutures. The sutures, however, induce astigmatism. The current trephine cutting techniques also produce tissue addition or tissue removal asymmetrically around the corneal periphery. These tissue aberrations further increase astigmatism.

Continuing efforts are being made to improve eye surgery methods and apparatus. Consider background patents which illustrate, for example, the large number of corneal transplant techniques such as in U.S. Pat. No. 3,945,054 to Fedorov and U.S. Pat. Nos. 4,772,283; 5,030,230 and 5,139,518 all to White.

In addition, apparatus including punches for preparing donor material for corneal transplants are disclosed in another large number of patents. By way of example, note U.S. Pat. No. 4,236,519 to La Russa; U.S. Pat. No. 4,824,066 to Smith; U.S. Pat. No. 4,718,420 to Lemp; U.S. Pat. No. 4,429,696 to Hanna; and U.S. Pat. No. 4,190,050 to Bailey.

Another grouping of background patents are those which disclose corneal layers used in association with eye surgery. By way of example, note U.S. Pat. No. 4,662,881 to Nordan; U.S. Pat. No. 3,454,966 to Rosen; and U.S. Pat. No. 4,810,082 to Abel.

Lastly, U.S. Pat. No. 4,127,903 to Schachar discloses an intraocular lens.

Efforts to improve eye surgery techniques continue. Accordingly, it is an object of the invention to provide an improvement which overcomes inadequacies of the prior art devices and provides an improvement which is a significant contribution to the advancement of the art.

Another object of the invention is to provide a new device that allows for penetrating keratoplasty with attendant corneal tabs.

A further object of the invention is to use corneal tabs from the donor material into the recipient rim.

A further object of the invention is to transplant corneas without sutures.

A further object of the invention is a more rapid completion of a corneal transplant.

A further object of the invention is reduced corneal astigmatism.

A further object of the invention is to improve wound healing following corneal transplant.

A further object of the invention is to reduce incidences of graft rejection following corneal transplants.

2

A further object of the invention is to improve wound coaptation following corneal transplants.

A further object of the invention is to transplant a cornea without sutures comprising (1) a donor material in the shape of a partial sphere having a central extent, the central extent being of the size and shape of the central portion of the cornea of the eye, the central extent having a periphery and an exterior surface in a convex configuration and an interior surface in a concave configuration and with an essentially common thickness throughout, the central extent having a plurality of corneal tabs extending radially from the periphery of the central extent, the tabs having exterior surfaces as a continuation of the exterior surface of the central extent and (2) a recipient eye in the shape of a partial sphere having an aperture in the cornea at its central portion, the aperture in the cornea being of a size and shape essentially that of the periphery of the central extent of the donor material, the central portion having pockets equal in number to the plurality of tabs of the donor material and aligned therewith, and with the central extent of the donor material located within the aperture of the recipient eye and with the tabs of the central extent being located within the respective pockets of the recipient eye.

A further object of the present invention is to provide an apparatus and method for repairing a cornea of an eye, comprising the steps of providing a donor material in the shape of a partial sphere, the donor material having an exterior Bowman's membrane; die cutting the donor material to define an outline configuration including a central extent and a plurality of tabs extending outwardly therefrom; shaving the Bowman's membrane of the tabs to remove donor material therefrom leaving the Bowman's membrane of the tabs intact with the Bowman's membrane of the central extent; forming a central aperture in the cornea to be repaired, the central aperture having a size and shape essentially that of the central extent of the donor material; incising a plurality of pockets from the central aperture into the cornea, the pockets being positioned and sized and shaped to receive the respective tabs when the central extent is positioned within the central aperture; and positioning the central extent within the central aperture and imbricating the tabs into the respective pockets.

The foregoing has outlined some of the pertinent objects of the invention. These objects should be construed to merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

For the purpose of summarizing the invention, the invention comprises an eye with a cornea repaired with minimal or no sutures including, in combination, a donor material and a recipient eye. The donor material is in the shape of a partial sphere and is cut in a generally circular central extent, the central extent being of the size and shape of the central portion of a cornea of an eye, the central extent having a periphery of a fixed diameter of between about 7.0 and 7.5 millimeters with an exterior surface in a convex configuration and an interior surface in a concave configuration and with an essentially common thickness throughout, the central extent having four to sixteen, preferably six, symmetrically positioned corneal tabs, preferably diamond-shaped, extending radially from the periphery of the central extent, the tabs having exterior surfaces as a continuation of the exterior surface of the central extent, and the exterior surfaces of the central extent and the tabs being of a common Bowman's membrane of about 100 microns thickness. Preferably, the tabs have a thickness of about 10 percent of the thickness of the central extent with the area of juncture between the tabs and the central extent constituting between about 10 percent and 100 percent (i.e., one continuous tab) of the circumference of the central extent, with the radial dimension of each tab being between about 25 and 75 percent of the diameter of the central extent, with the side edges of the tabs being radii of the central extent, and with the radially exterior edge of each tab being curved concentric with the curvature of the central extent. The recipient eye is in the shape of a partial sphere having a circular aperture in the cornea at its central portion, the circular aperture being of a size and shape essentially that of the periphery of the central extent of the donor material, the aperture being of a common thickness at the periphery of the aperture, the central portion having four to sixteen, preferably six, symmetrically positioned pockets, with the pockets being at the area adjacent to the periphery of the aperture and constituting between about 10 percent and 100 percent (i.e., one continuous tab) of the periphery of the aperture, and with the radial dimension of each pocket being between about 25 and 75 percent of the diameter of the aperture. The central extent of the donor material is positioned within the aperture of the recipient eye, and then the tabs of the central extent are imbricated into the respective pockets of the recipient eye.

Advantageously, corneal transplantation according to the invention permits elevated intraocular pressure without tissue movement. Further, the imbrication of the tabs into the pockets reduces astigmatism in the postoperative period.

The invention of this continuation-in-part patent application is directed to an outline cutter assembly comprising male and female dies for die-cutting the outline of the donor material inclusive of the central extent and the tabs when the donor material is placed therebetween and the dies are mated. The outline cutter assembly further includes a tab incisor punch for annularly cutting through the donor material about the periphery of the central extent from the interior surface thereof to a depth proximate of the common Bowman's membrane such that the Bowman's membrane of the central extent and the tabs remains intact. The invention of this continuation-in-part patent application is also directed to a tab shaver assembly comprising male and female dies for folding the tabs of the die-cut and incised donor material along the length of the male die when the die-cut and incised donor material is placed therebetween and the dies are mated. The tab shaver assembly further includes a tab shaver punch for inserting between the mated dies to annularly shave the donor material from the Bowman's membrane of the folded-back tabs. The Bowman's membrane of the tabs therefore remains intact with the Bowman's membrane of the central extent. The die-cut and shaved donor material may now be utilized in the transplantation method of the invention as described above.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 2 is an exploded perspective view of the eye illustrated in FIG. 1;

FIG. 8 is an exploded view of the outline cutter assembly of the invention illustrating the base support, hand support, tab incisor punch, and spring-loaded medical syringe;

FIG. 9A is a longitudinal cross-sectional view of the male die of the outline cutter assembly illustrating the longitudinal cross-sectional configuration of the male die;

FIG. 9B is a longitudinal cross-sectional view of FIG. 9A taken within the longitudinal slots thereof illustrating the longitudinal cross-sectional configuration of the male die;

FIG. 9C is a transverse cross-sectional view of the upper portion of the male die illustrating the transverse cross-sectional configuration of the male die;

FIG. 15 is an exploded diagram of the tab shaver assembly of the invention illustrating the base support, hand support, the tab shaver punch and the spring-loaded medical syringe thereof;

FIG. 18 is a cross-sectional view of the male die of the tab shaver assembly taken through the upstanding arms thereof.

Similar reference characters refer to similar parts throughout the several views of the drawings.

DETAILED DESCRIPTION OF THE PREFERRED EMBODIMENT

Eye With Transplanted Cornea

Figure 1:
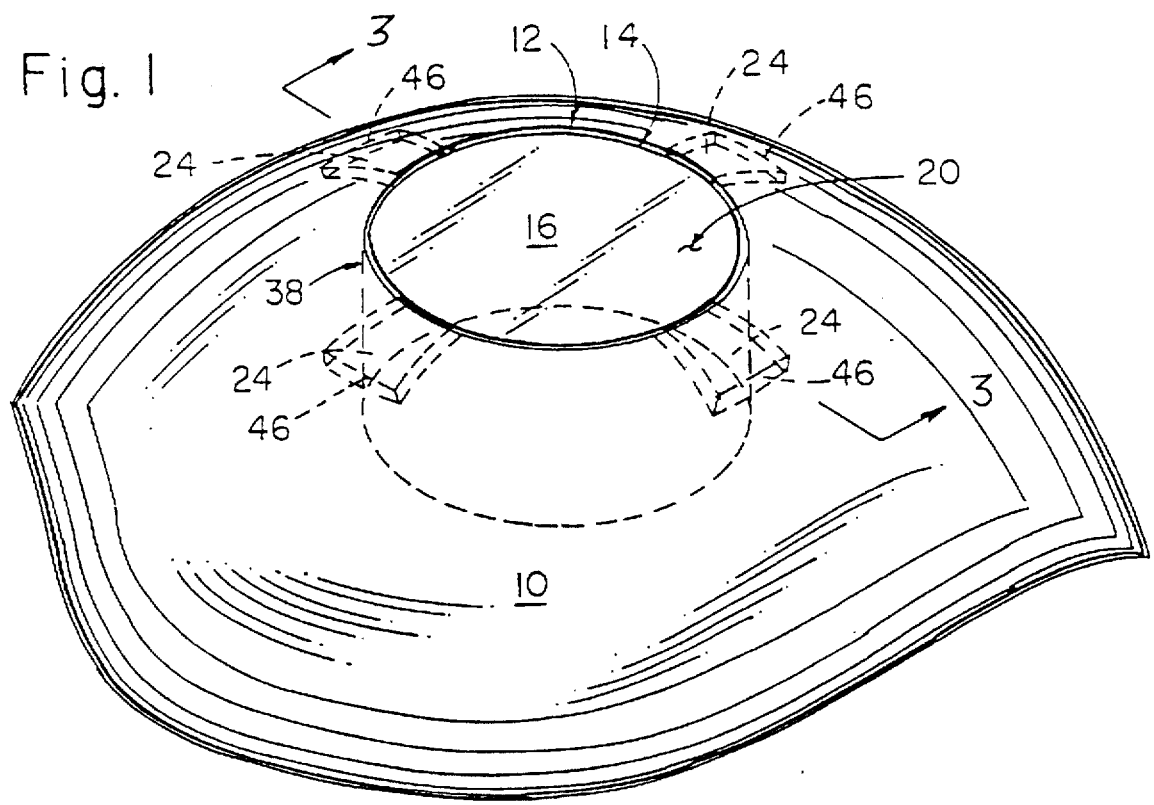
FIG. 1 is a perspective illustration of the preferred embodiment of a sutureless corneal transplant effected in accordance with the principles of the present invention.

The present invention as illustrated in FIGS. 1 and 2 relates to an eye 10 with a cornea 12 repaired with minimal or no sutures. The repaired cornea 12 includes two major components, the donor material 14 and the recipient eye 10.

With regard to the donor material 14, such material is cut to a particular shape prior to being coupled with the recipient eye 10. The shape is that of a partial sphere. Such sphere has a generally circular central extent 16. The central extent 16 is of the size and shape of the central portion of the cornea of an eye. The central extent 16 has a periphery 18 of a fixed diameter of about 7.0 and 7.5 millimeters. It has an exterior surface 20 in a convex configuration. It also has an interior surface 22 in a concave configuration. The central extent 16 also has an essentially common thickness throughout.

Formed as part of the central extent 16 are a plurality of symmetrically positioned diamond-shaped corneal tabs 24. Four to sixteen of such tabs is the preferred number and six is the most preferred. Such tabs 24 extend radially from the periphery 18 of the central extent 16. The tabs 24 have exterior surfaces 26 as a continuation of the exterior surface 20 of the central extent 16. The exterior surfaces 20 and 26 of the central extent 16 and tabs 24, respectively, are preferably of a common Bowman's membrane 28 typically having a thickness of about 100 microns.

The tabs 24 typically have a thickness of about 10 percent of the thickness of the central extent 16 of the donor material. The radial dimension of each tab 24 is between about 25 and 75 percent of the diameter of the central extent 16. The side edges 32 of the tabs 24 are preferably formed as radii of the central extent 16. In addition, the radially exterior edges 34 are preferably curved essentially concentric with the curvature of the central extent 16.

The next component of the repaired cornea is the recipient eye 10. Such eye 10 is in the shape of a partial sphere. The recipient eye 10 is formed with a circular central aperture 38 at its central portion 40. The circular central aperture 38 is of a size and shape essentially that of the periphery 18 of the central extent 16 of the donor material 14 for the receipt thereof. The periphery 42 of the aperture 38 is of a common thickness. The central portion 40 has a plurality (four illustrated) of symmetrically positioned pockets 46. The pockets 46 are simply incisions made into the thickness of the cornea, preferably just under the Bowman's membrane 28 into the periphery 42 of the aperture 38. The pockets 46 each constitute between about 10 and 100 percent of the periphery 42 of the aperture 38. The radial dimension of each pocket 46 is between about 25 and 75 percent of the diameter of the aperture 38.

In operation and use, the central extent 16 of the donor material 14 is positioned within the aperture 38 of the recipient eye 10. The tabs 24 of the central extent 16 are imbricated into the pockets 46 of the recipient eye 10. Forceps are preferably used for the positioning of the central extent 16 and the imbrication of each of the tabs 24 into their respective pockets 46.

Transplantation Method

The invention, in addition to the combination of the donor material 14 and recipient eye 10, also includes the method of repairing the recipient eye 10. Such method includes the step of providing donor material 14 of the type as described above. The method also includes the step of providing a recipient eye 10 as described above. The method then includes a step of positioning the donor material 14 with its central extent 16 within the aperture 38 of the recipient eye 10 and imbricating the tabs 24 of the donor material 14 into the pockets 46 of the recipient eye 10.

The invention further comprises a method for preparing the donor material 14 and for preparing the recipient eye 10. More particularly, the central extent 16 and the tabs 24 are preferably cut out of the donor material 14 obtained from a donor's eye (not shown). Such cuts are preferably made by first inverting the donor material 14 and resting its convex exterior surface 20 onto a suitable support and then holding it into position by means of vacuum or the like. The cuts are then made through the donor material 14 in an outline configuration to produce the central extent 16 with the plurality of tabs 24. Preferably, such cuts are made parallel to the axis of the partial sphere of the central extent 16. Additional cuts are then made at the juncture between the central extent 16 and the tabs 24 to a depth of about 90 percent of the thickness of the central extent 16, thereby leaving intact the common Bowman's membrane 48 of the central extent 16 and the tabs 24 that constitutes the convex exterior surfaces 20 and 26 of the central extent 16 and the tabs 24, respectively. Finally, additional cuts are made parallel along the Bowman's membrane 28 constituting the exterior surface 26 of the tabs 24 so as to remove the corneal material from the tabs 24 while leaving intact the Bowman's membrane 28 of the tabs 24 and the central extent 16.

Figure 3:
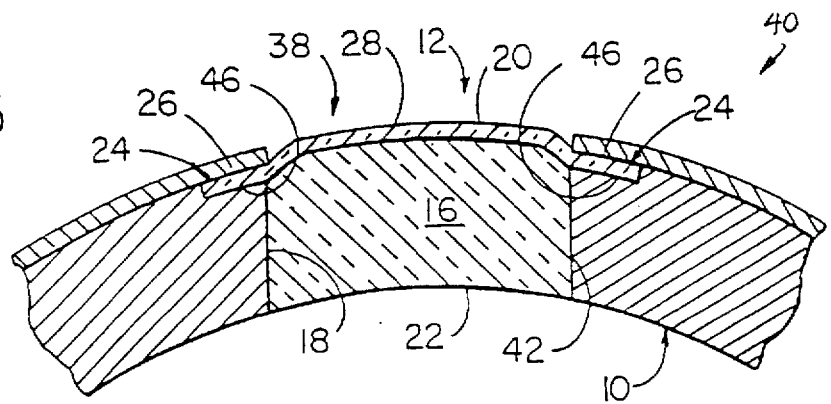
FIG. 3 is a cross-sectional view of the repaired eye of FIG. 1.

The recipient eye 10 is prepared according to the method of this invention by first marking the intended location of the pockets 46 with a conventional corneal marking tool (not shown). The circular aperture 38 is then cut into the central portion 40 of the recipient eye 10 by means of a conventional trephine or the like (not shown) which makes a circular cut through the central portion 40 whereupon the central portion 40 of the recipient eye 10 is removed and discarded. The pockets 46 are then formed into the periphery 42 of the central aperture 38 and the recipient eye 10 by means of a conventional diamond knife (not shown) having a width equal to the proximal width of the openings of the pockets 46 intended to be formed in the periphery 42 of the circular aperture 38. Each pocket 46 is then formed by inserting the diamond knife into the periphery 42 of the central aperture 38 of the recipient eye 10 in alignment with the respective corneal markings previously made. As shown in FIG. 3, the knife is preferably positioned just under the Bowman's membrane and then advanced inwardly to a depth equal to the intended depth of the pocket 46. The diamond knife is then moved in both directions sideways so as to cut a diamond-shaped pocket corresponding to the size and shape of the tabs 24. It is noted, however, that the width of the diamond knife and hence the width of the opening into the pockets 46 may be appreciably smaller than the corresponding width of the tabs 24 at its juncture with the central extent 16 so as to more securely retain the tabs 24 in the pockets 46.

After preparing the donor material 14 and the recipient eye 10 in the manner described above, the donor material 14 may then be coupled with the recipient eye 10 by positioning the central extent 16 of the donor material 14 into the central aperture 38 of the recipient eye 10. Each of the tabs 24 are imbricated into the respective pockets 46 by means of forceps which, when pressed upon each of the tabs 24, cause the tabs 24 to fold, thereby facilitating the insertion of the tabs 24 into their respective pockets 46. After all of the tabs 24 are positioned within their respective pockets 46, the central extent 16 is securely retained within the central aperture 38 of the recipient eye 10 in such a manner that postoperative astigmatism is minimized while permitting increased intraocular pressure without tissue movement.

Figure 3A:
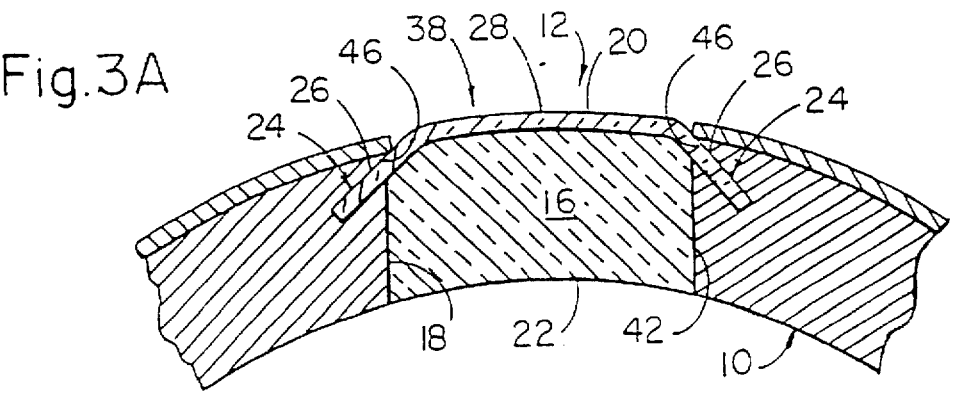
FIG. 3A is a cross-sectional view of the repaired eye of FIG. 1 but with the pockets in the recipient eye being positioned further interiorly.
Figure 4:
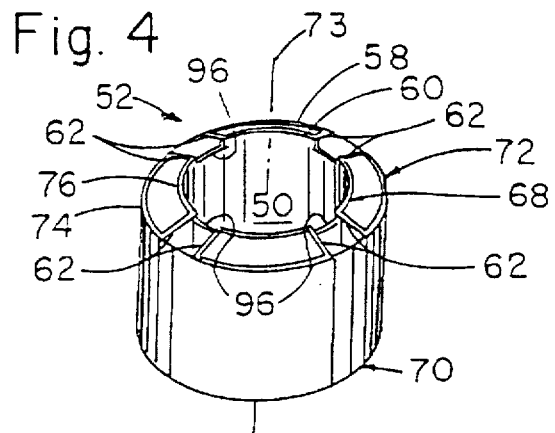
FIG. 4 is a perspective illustration of a trephine for use in association with the sutureless corneal transplant technique of the present invention.
Figure 5:
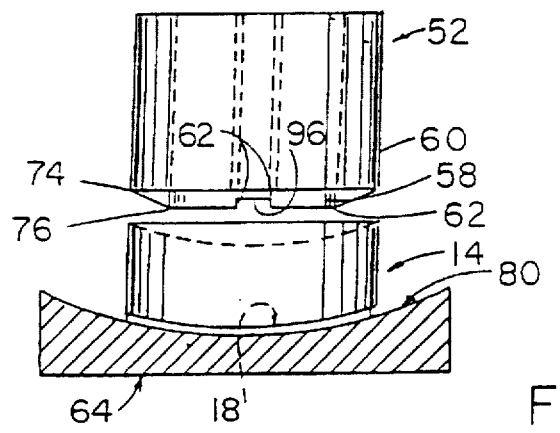
FIG. 5 is a side elevational view of the trephine of FIG. 4 and an associated block.
Figure 6:
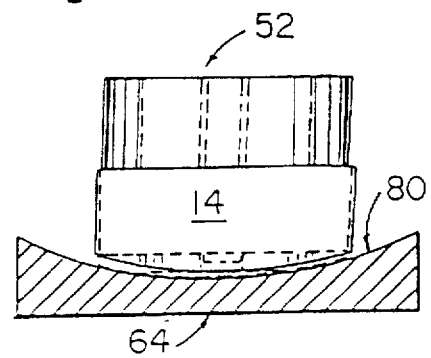
FIG. 6 is a side elevational view similar to FIG. 5 but showing the trephine during the cut.
Figure 7:
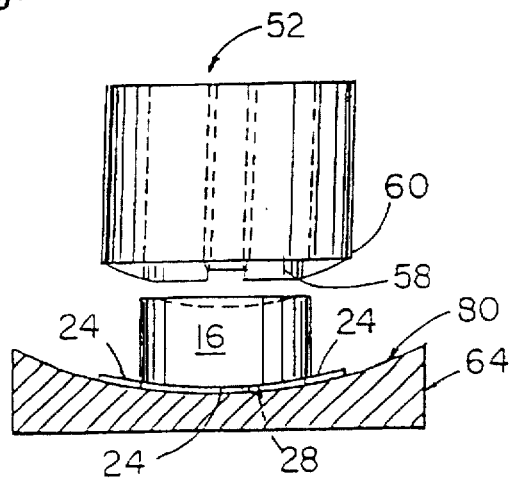
FIG. 7 is a side elevational view similar to FIGS. 5 and 6 but showing the trephine in the retracted position after the cut.

It is noted that if the width of the openings of the pockets 46 were incised appreciably smaller than the width of the tabs 24 at their juncture with the central extent 16, as described above, the tabs 24 may be more securely retained therein by forming a notch or otherwise nicking the tabs 24 at their juncture with the central extent 16 thereby allowing the narrower-width edges of the pocket openings to engage therein. It is also noted that to minimize astigmitation due to swelling, the pockets 46 may be cut further interiorally as shown in FIG. 3A. Without departing from the spirit of the invention, in the event that the donor material 14 shifts post operatively due to trauma or otherwise, the tabs 24 may be temporarily secured in the respective pockets 46 by means of sutures.

It is noted that the transplantation method of this invention is not limited to corneal transplantation and may be implemented in other transplantations without departing from the spirit and scope of this invention.

Transplantation Trephine and Method of Use

In addition to the eye with a repaired cornea and the method of repairing a cornea as set forth above, the present invention also includes a trephine 52.

The trephine 52 of the invention is particularly useful in cutting and forming the donor material 14 as described above. The trephine 52 of the invention is for the cutting of donor material 14 and is adapted to be used in corneal transplants. The trephine 52 comprises, in combination, a cylindrical support 56, a plurality of circular cutting blades 58 and 60, radially extending blades 62 and an associated block 64.

More specifically, the cylindrical support 56 of the invention is adapted to be held by a surgeon in the cutting of the donor material 14. The trephine 52 includes a cylindrical central portion 68 with an upper edge 70 and a lower edge 72. A central axis 73 extends along the length of the cylindrical support 56.

The plurality of circular cutting blades 58 and 60 are formed in the lower edge 72 of the cylindrical support 56. The circular cutting blades 58 and 60 include an exterior continuous cutting blade 74 having a diameter between about 11 and 12 millimeters. The cutting blades 58 and 60 also include an interior discontinuous cutting blade 76 having a diameter of about between 7 and 7½ millimeters.

The radially extending blades 62 are located between the circular blades 58 and 60. The exterior circular blade 60 is located closer to the upper edge 70 of the cylindrical support 56 than the interior circular blade 58 by a distance of about 100 microns equal to the thickness of the Bowman's membrane 28. The radial blades 62 thus extend at an acute angle with respect to the upper edge 70 of the support 56. For producing four tabs 24, the radial blades 62 are eight in number and arranged for cutting diamond shaped tabs 24. The tabs 24 together constitute between about 10 and 100 percent of the circumvents of the inner and outer circular blades 58 and 60. The radially interior edge 96 of the interior cutting blade 76 is blunt to preclude cutting of donor material 14 at the location of the tabs 24.

In association with the above trephine 52, there is provided a block 64. Such block 64 has a pocketed, generally spherical surface 80. Such spherical surface has a radius of curvature of about 7.5 millimeters. The purpose of such surface is for constituting a support for the donor material 14 during the cutting thereof by the trephine 52.

The use of the trephine 52 as described above constitutes an inventive method of the invention in addition to the trephine 52 itself. In practicing the method of cutting donor material 14 with the trephine 52 as described above, the steps include providing a cylindrical support 56 of the type as described above. The method then includes the step of providing a plurality of circular cutting blades 58 and 60 in the cylindrical support 56 as described above. The method also includes the step of providing radially extending blades 62 between the circular blades 58 and 60 as described above. The invention also includes the step of providing an associated block 64 as described above. The method of the invention then includes the step of positioning donor material 14 adapted to be used in corneal transplants on the support surface 80 of the block 64 and cutting such supported donor material 14 with the trephine 52 as described above.

In the fabrication of the pockets 46 in the recipient eye 10, the incisions which extend generally parallel with the upper and lower surfaces of the eye 10 beneath the Bowman's membrane 28 are preferably done by a conventional diamond knife in the manner described above.

The specifics of the trephine 52 as described above are as follows:

A trephine blade which punches out the donor material to 90 percent of the corneal thickness;

A trephine blade which punches out the donor material at a rim of 10–12 millimeters;

A diamond incision of the superficial Bowman's membrane which fashions corneal tabs for insertion into the recipient rim;

A recipient rim formation beneath the Bowman's membrane of a pocket through which the donor tab is transferred;

The method of securing the donor tab in the recipient rim is with forceps that allow manipulation of the tabs in the postoperative period to reduce the astigmatism and to allow for a spherical surface;

The lack of sutures at the time of corneal transplantation reduces the need for suture adjustment and the attendant micro abscesses and wound compression that occur with all sutures;

The recipient bed is incised in a step fashion to coapt the stroma;

A diamond knife is provided which produces an undermined tab of Bowman's membrane;

A corneal punch which produces donor tabs of Bowman's membrane; and

Forceps for insertion of the Bowman's membrane tabs beneath the recipient rim.

Outline Cutter Assembly, Tab Shaver Assembly and Method of Use

The invention of this continuation-in-part patent application comprises an outline cutter assembly 100 as shown in FIGS. 8–14 for cutting the outline of the donor material 14 inclusive of the central extent 16 and the tabs 24 and a tab shaver assembly 102 as shown in FIGS. 15–18 for shaving the tabs 24 to remove the corneal material from the tabs 24 leaving the Bowman's membrane 28 of the tabs 24 intact with the Bowman's membrane 28 of the central extent 16.

More particularly, the outline cutter assembly 100 shown in FIGS. 8–14 comprises a male die 104 rigidly extending vertically from a generally-rectangular base support 106, a female die 108 rigidly supported within a hand support 110 and a tab incisor punch 112. As best shown in FIGS. 9A–9D, the male die 104 comprises a generally circular cylindrical member 114 having an increased diameter upper portion 116 and a reduced diameter lower portion 118. Equally-spaced slots 120 are machined longitudinally along the length of the upper portion 116. Slots 120 are configured and dimensioned such that the cross-sectional configuration (see FIG. 9C) of the upper portion 116 of the male die 104 is the same as the desired outline configuration of the donor material 14 inclusive of its central extent 16 and tabs 24.

For example, when desired to produce a six-tabbed donor material 14, the upper portion 116 of the cylindrical member 114 is machined with six equally-spaced slots 120. Furthermore, when desiring to produce tabs 24 having radial side edges 32 as described above, the sides 122 of slots 120 may be machined as radii of the cylindrical member 114. Finally, with the outer diameter of the upper portion 116 of the cylindrical member 114 being determined to equal the desired outer diameter of the donor material 14, the depth at which the slots 120 are machined into such upper portion 116 determines the outer diameter of the central extent 16 of the donor material 14 and thus, the relative size of its tabs 24.

The upper end 126 of the upper portion 116 of the cylindrical member 114 is machined concavely to a partially-spherical configuration having a radius substantially equal to the spherical radius of the exterior surface 20 of the donor material 14. It is noted that the spherical machining of the upper end 126 creates upwardly extending sharp edges 128 in an outlined configuration of the slotted upper end 126 of the upper portion 116 of the cylindrical member 114. As will become apparent below, the sharp edges 128 serve to cut the donor material 114 in an outline configuration inclusive of its central extent 116 and tabs 24.

The male die 104 preferably includes a central blind hole 104B extending from its lower portion 118 and into its upper portion 116, and a plurality of suction holes 104S extending from the blind hole 104B to the surface of its upper end 126. When a source of vacuum is fluidly connected to the blind hole 104B and the donor material 14 is positioned on the upper end 126, the vacuum in the suction holes 104S assures that the donor material 14 will remain securely seated.

Figure 10A:
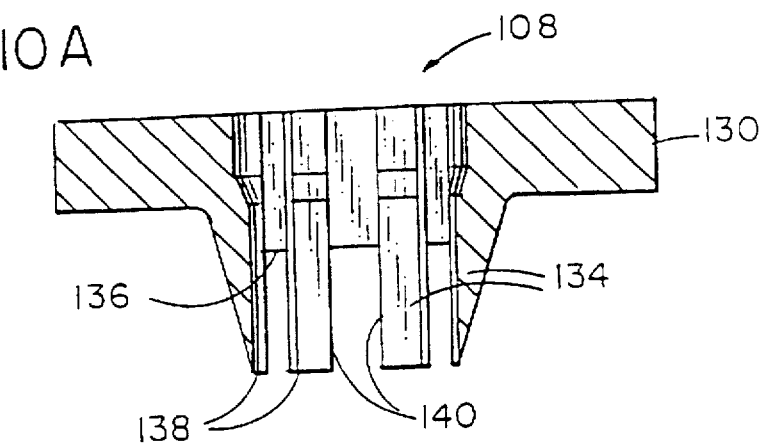
FIG. 10A is a longitudinal cross-sectional view of the female die of the outline cutter assembly of the invention taken through the cutting teeth thereof.
Figure 10B:
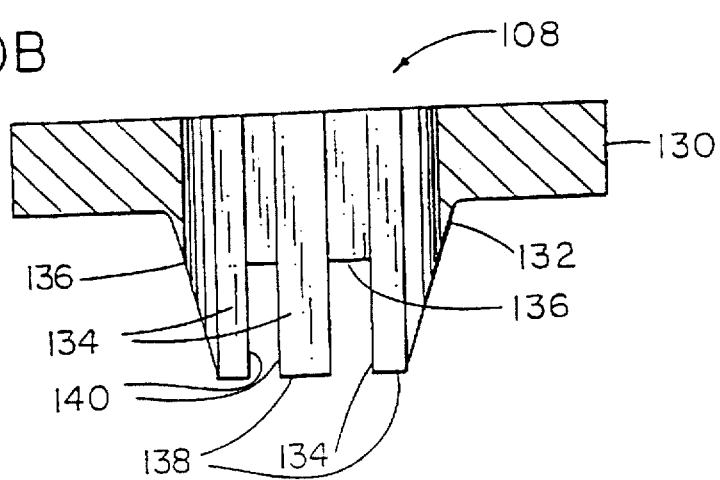
Fig. 10B is a longitudinal cross-sectional view of the female die taken between the cutting teeth thereof.

Corresponding to the male die 104, as best shown in FIGS. 10A and 10B, the female die 108 comprises a generally circular cylindrical member 130 having an annular cutting rim 132 with cutting teeth 134 extending downwardly therefrom. The radially outward surfaces of the annular cutting rim 132 and the cutting teeth 134 are frustro-conically shaped such that the lowermost edge 136 of the cutting rim 132 and the lowermost edges 138, as well as side edges 140, of the cutting teeth 134 define sharp cutting edges.

It is noted that the cutting teeth 134 of the female die 108 are appropriately configured and dimensioned to axially mate with and slide into the slots 120 formed in the upper portion 116 of the male die 104 such that when the donor material 14 is positioned therebetween and the dies 104 and 106 are axially mated together, the donor material 14 is precisely die-cut into the desired outline configuration.

Notably, the frustro-conical shape of the cutting teeth 134 as well as the cutting rim 132 assures that the donor material 14 is cylindrically cut even though the donor material 14 (and the upper end 26 of the male die 104) are partially spherically shaped.

Figure 11:
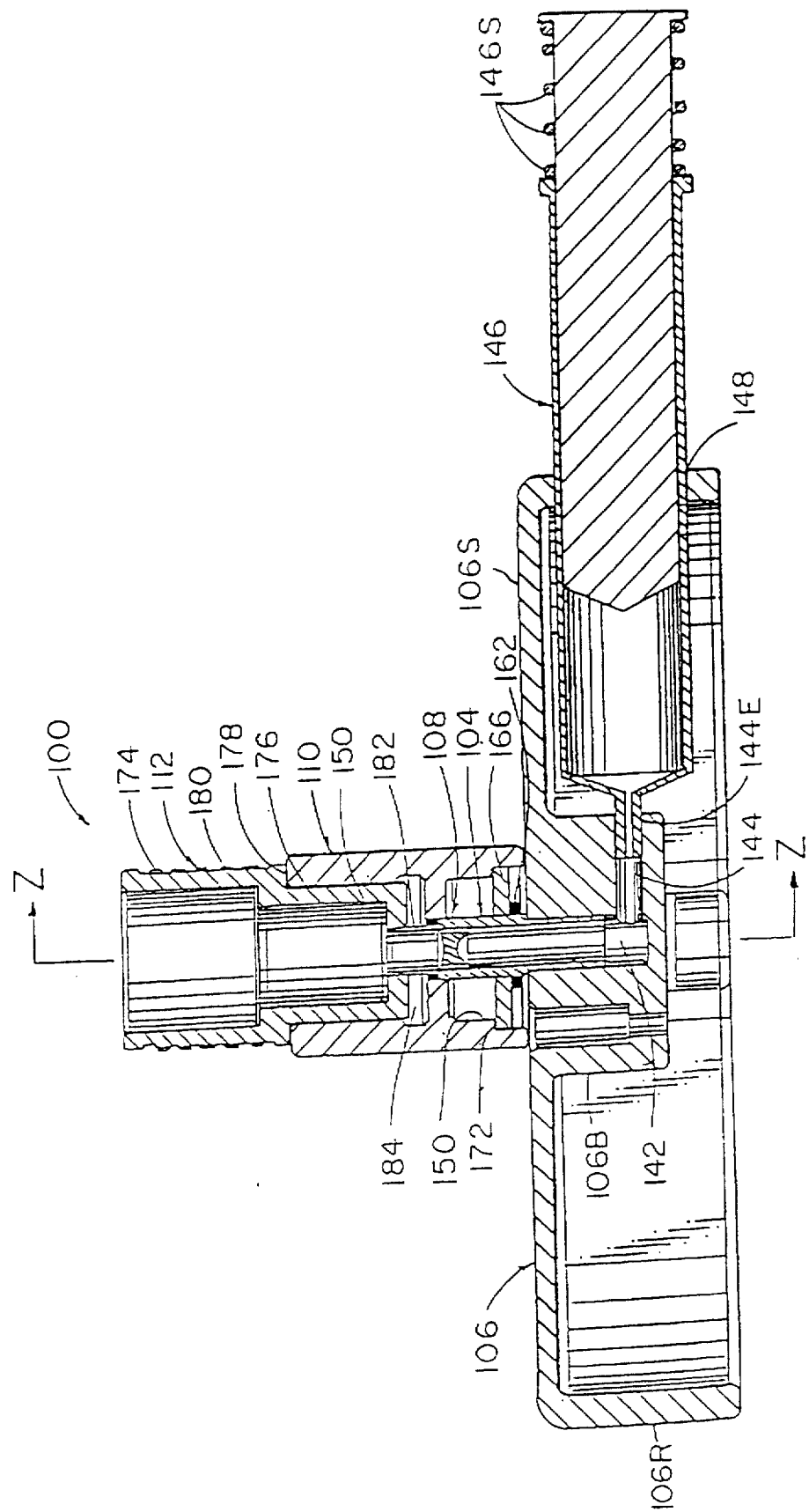
FIG. 11 is a longitudinal cross-sectional view of FIG. 8 illustrating the spring-loaded medical syringe rigidly connected to the access and vacuum holes of the boss of the base support for creating vacuum within the male die.
Figure 12:
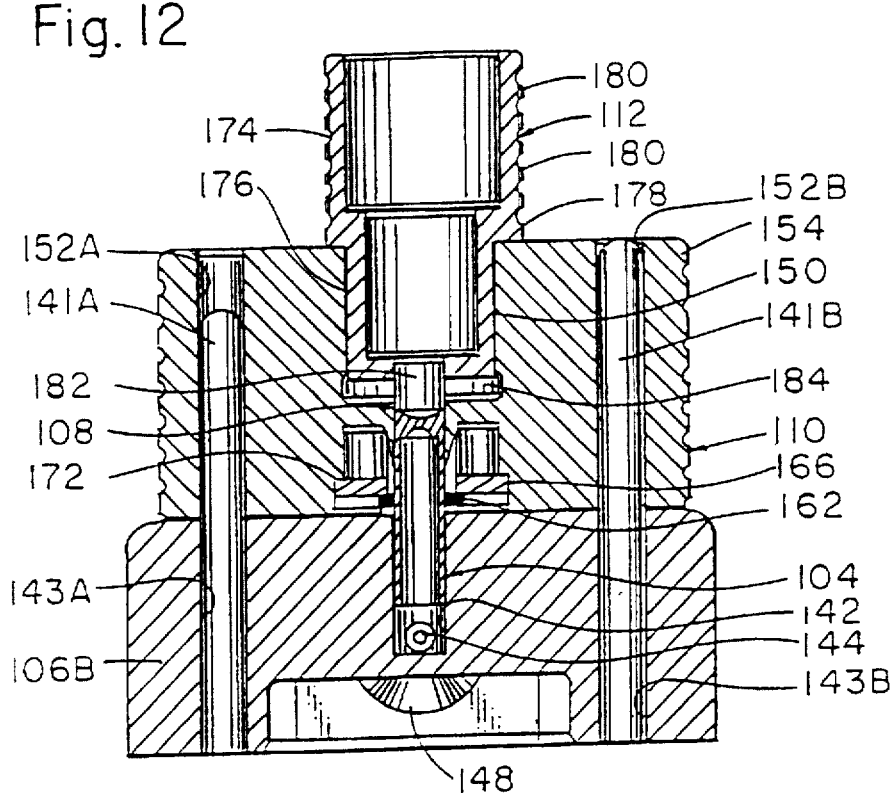
FIG. 12 is a transverse cross-sectional view of FIG. 8 illustrating the guide pins that axially guide the hand support containing the female die in axial engagement with the male die extending from the base support.

Notably, as best shown in FIG. 8 in combination with FIGS. 11 and 12, in order to assure exact axial mating of the male and female dies 104 and 108, the male die 104 is supported by the base support 106, female die 108 is supported by the hand support 110 and the supports 106 and 108 are axially movable relative to one another by means of guide pins 141A and 141B.

More particularly, base support 106 comprises a generally hollow rectangular configuration defined by rim 106R and a flat top surface 106S from which a boss 106B interiorly extends. The lower portion 118 of the cylindrical member 114 of the male die 104 is rigidly positioned into a cylindrical blind hole 142 in the boss 106B of the base support 106. Blind hole 142 is formed at a right angle to the flat upper surface 106S of the base support 106 such that the upper portion 116 of the male die 104 extends perpendicularly therefrom. The guide pins 141A and 141B, preferably of different diameters and heights, are rigidly mounted into guide holes 143A and 143B in the boss 106B of the base support 106 so as to extend parallel to each other and to the male die 104.

A vacuum hole 144 extends from the exterior of the boss 106B to the blind hole 142. Its opened end 144E is dimensioned to be fitted with a source of vacuum, such as a spring-loaded medical syringe 146. It is noted that the spring 146S of such a spring-loaded medical syringe 146 preferably includes a spring constant that creates the desired vacuum within the blind and vacuum holes 142 and 144 (and correspondingly the male die 104) so as to assure that the donor material 14 is held in its seated position within the spherical upper end 126 of the male die 104. Conveniently, access hole 148 formed in the rim 106R of the base support 106 supports the syringe 146 in collinear alignment with the vacuum hole 144.

The hand support 110 in which is positioned the female die 108 (or formed integrally therewith as shown), comprises a central bore 150 for receiving the female die 108 and a pair of side bores 152A and 152B for slideably receiving the guide pins 141A and 141B of the base support 106. The central bore 150 is positioned relative to the side bores 152A and 152B such that the female die 108 is positioned in precise axial alignment with the male die 104 when the guide pins 141A and 141B are positioned into the respective side bores 152A and 152B, thereby permitting the female die 108 to axially engage the male die 104 as shown in FIGS. 11 and 12 with the hand support 110 eventually being seated on the upper surface 106S of the base support 106.

Indeed, it should be appreciated that the longitudinal positioning of the female die 108 within the central bore 150 determines the extent by which the female die 106 mates with and extends along the length of the upper portion 116 of the male die 104. Finally, it should be appreciated that the hand support 110 comprises a substantially oblong configuration that can be easily grasped by the physician performing the corneal transplantation and then conveniently oriented and aligned with the base support 106 such that the guide pins 141A and 141B engage into the side bores 152A and 152B, respectively. As shown, the outer exterior surfaces of the hand support 110 may be knurled 154 to facilitate better grasping of the hand support 110 by the physician.

Figure 13:
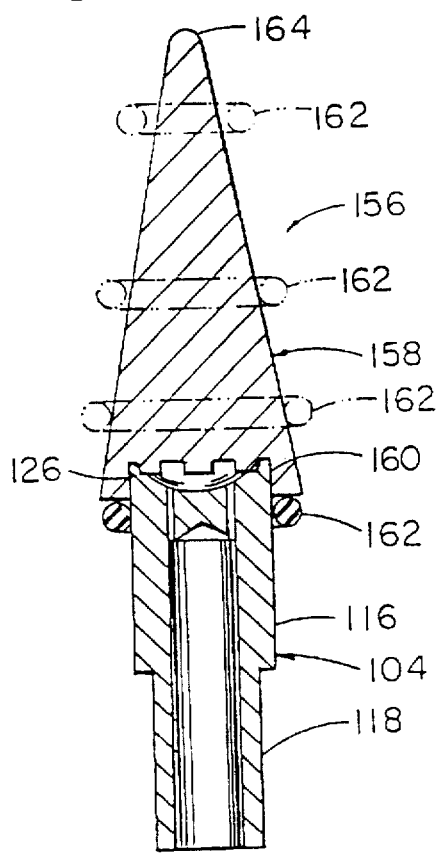
FIG. 13 is a longitudinal cross-sectional view of the male die of the outline cutter assembly with the spreader tool of the donor material support assembly positioned thereon for facilitating positioning of the O-ring about the male die.
Figure 14:
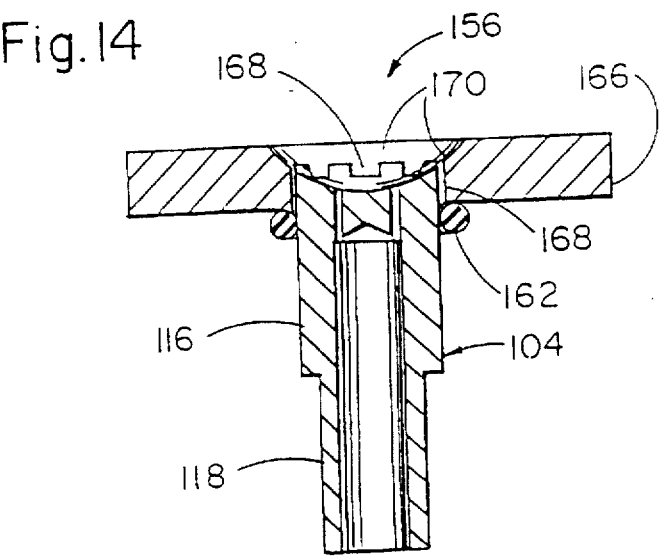
FIG. 14 is a cross-sectional view of the male die of the outline cutter assembly with the donor material supporter of the donor material support assembly held into position about the upper end of the male die by means of the O-ring.

As best shown in FIGS. 13 and 14 in combination with FIG. 8, a donor material support assembly 156 is preferably provided to provide additional support to the donor material 14 when it is positioned onto the upper end 126 of the male die 104 prior to cutting. More particularly, as shown in FIG. 13, the donor material support assembly 156 comprises a generally frustroconical spreader tool 158 having a recess 160 formed at its wide, lower end. The spreader tool 158 facilitates the positioning of an O-ring 162 onto the male die 104 by simply positioning the recessed end 160 of the spreader tool 158 onto the upper end 126 of the male die 104 and then positioning an O-ring 162 about the tip 164 of the spreader tool 158. By sliding the O-ring 162 along the length of the spreader tool 158 (as shown in phantom in FIG. 13), it is forced to expand. Once the O-ring 162 is slid past the recessed end 160 of the spreader tool 158, it resiliently grasps around the male die 104.

As shown in FIG. 14, an annular-shaped donor material supporter 166 with central hole 168 may then be positioned about the male die 104 and rested upon the O-ring 162. It is noted that the upper portion of the central hole 168 may be spherically recessed 170. In this manner, the depth of the recessed end 160 of the spreader tool 158 may be dimensioned such that the O-ring 162 is positioned about the male die 104 at a location that aligns the spherical recess 170 of the supporter 166 with the spherical upper end 126 of the male die 104. Importantly, the donor material supporter 166 assures that the donor material 14 retains its spherical shape while it is being die cut by the male and female dies 104 and 108. However, it is also noted that as the female die 108 is moved along the male die 104, the O-ring 162 and the donor material supporter 166 are easily pushed downwardly further along the length of the male die 104. Indeed, as best shown in FIGS. 11 and 12, central bore 150 of the hand support 110 may include a step portion 172 substantially equal in diameter to the diameter of the supporter 166. Step portion 172 is preferably positioned within the central bore 150 at a position slightly below the sharp edges 138 of the cutting teeth 134 of the female die 108 such that the supporter 166 is forced downwardly by means of the step portion 172 without actually engaging the sharp edges 138 and possibly dulling the same.

As best shown in FIGS. 11 and 12, the tab incisor punch 112 of the outline cutter assembly 100 functions to incise the circular configuration of the central extent 16 from the concave interior surface 22 thereof up to the Bowman's membrane 28 constituting the convex exterior surface 20 thereof. More particularly, the tab incisor punch 112 comprises a generally circular cylindrical configuration having an increased diameter portion 174 and a reduced diameter portion 176 that form a step 178 therebetween. A knurl 180 is formed about the outer surface of the increased diameter portion 174 to facilitate it functioning as a handle for easy grasping by the physician. The reduced diameter portion 176 is dimensioned to slideably engage into the upper portion of the central bore 150 of the hand support 110.

An annular cutter 182 extends concentrically from the bottom 184 of the reduced diameter portion 176. Preferably, the annular cutter 182 is frustro-conically shaped such that its cylindrical lumen is positioned parallel and concentrically with the axis of the punch 112. Finally, it is noted that the relative lengths of the annular cutter 182, the reduced diameter portion 176, the central bore 150 are such that the sharp edge of the annular cutter 182 is positioned away from the spherical recess of the end 126 of the male die 104 by thickness of the Bowman's membrane 28 (e.g., 100 microns) when the hand support 110 is seated on the surface 106S of the base support 106 and when the step portion 172 is engaged with the upper edge of the central bore 150. Consequently, after the outline of the donor material 14 is die cut by means of the male and female dies 104 and 108, the incisor punch 112 can be easily inserted into the central bore 150 of the hand support 110 and moved downwardly until seated. When seated, a precise cut is made about the periphery of the central extent 16 through the thickness thereof up to the Bowman's membrane 28 thereof. The Bowman's membrane 28 of the central extent 16 and the tabs 24 therefore remains intact. The donor material 14 may then be removed from the outline cutter assembly 100 by removing the incisor punch 112 and the hand support 110 and releasing the vacuum. The donor material 14, now outlined die-cut, may then be positioned within the tab shaver assembly 102 of the invention to shave off the excess donor material proximate to the Bowman's membrane 28 of the tabs 24.

Figure 17:
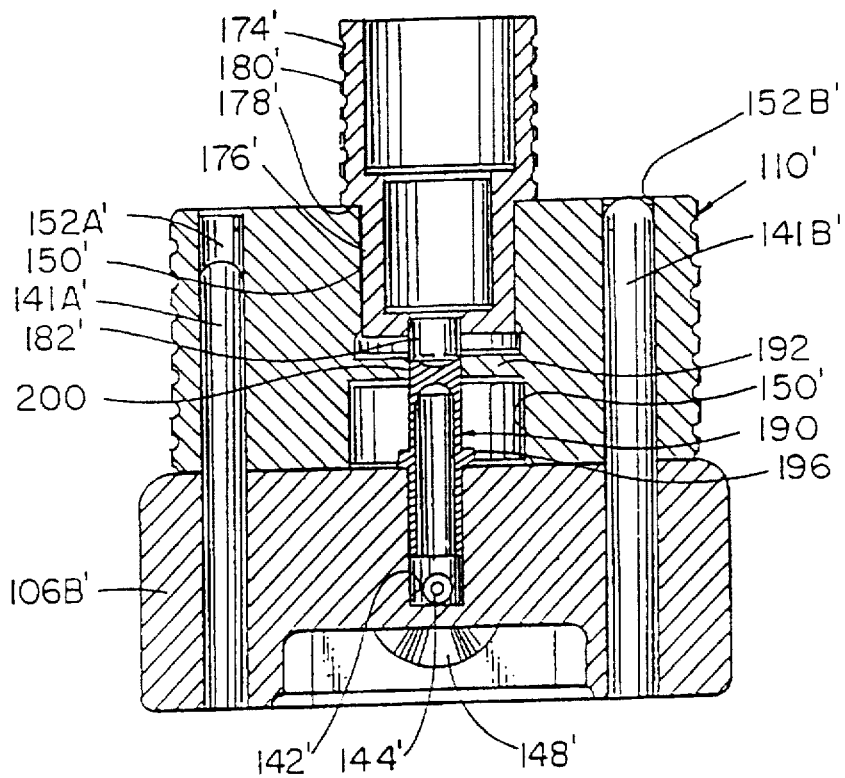
FIG. 17 is a transverse cross-sectional view of FIG. 15.
Figure 16:
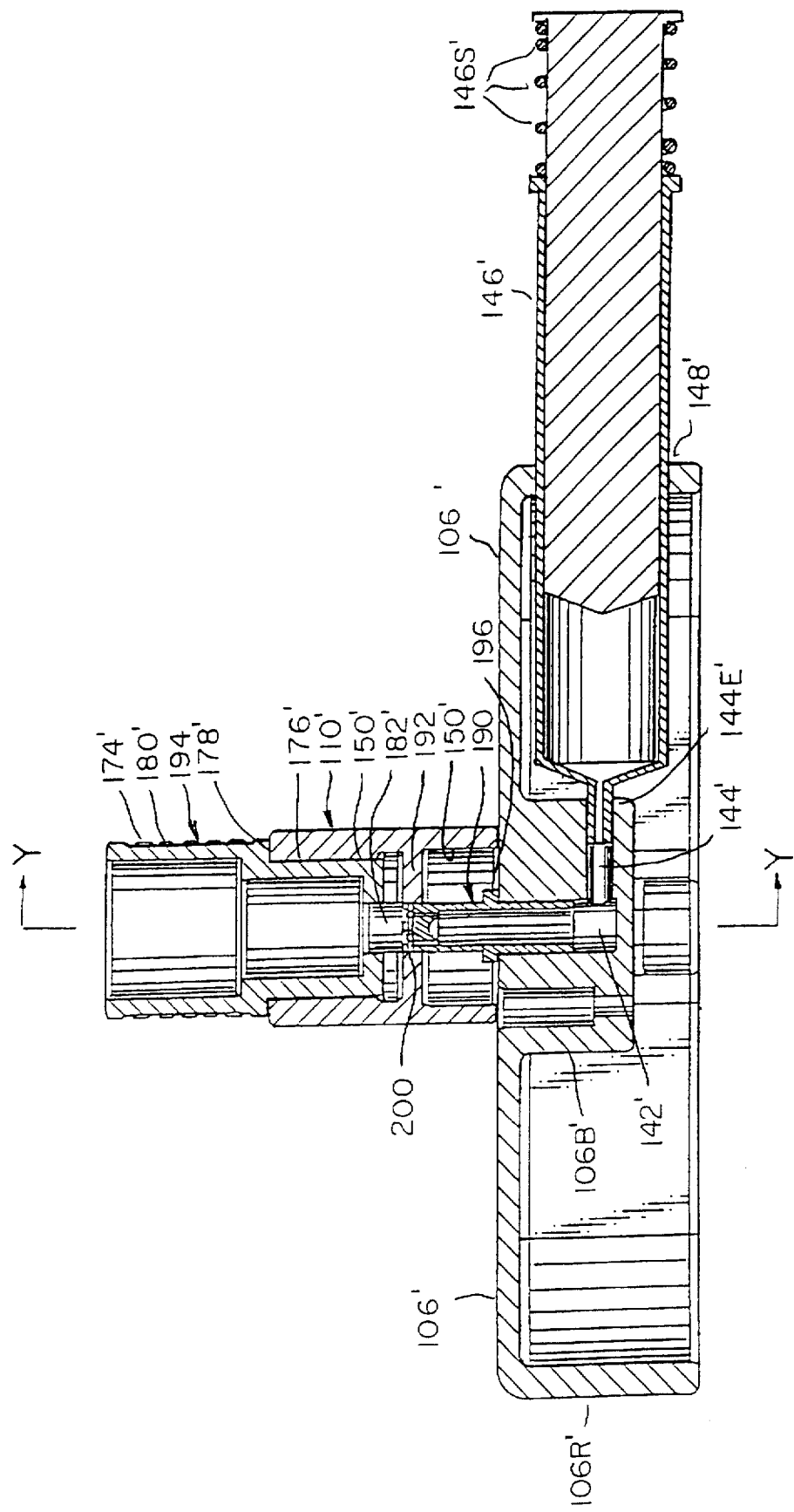
FIG. 16 is a longitudinal cross-sectional view of FIG. 15.

The tab shaver assembly 102 of the invention is illustrated in FIGS. 15-18 and comprises a vertically-disposed male die 190 that supports the outline die-cut donor material 14, a female die 192 that bends the tabs 24 of the donor material 14 downwardly along the length of the male die 190 when the dies 190 and 192 are engaged, and a tab shaver punch 194 that shaves the excess donor material from the tabs 24 while leaving the Bowman's membrane 28 intact. As shown in FIGS. 15, 16 and 17, many components of the tab shaver assembly 102 are similar to the corresponding components of the outline cutter assembly 100. Therefore, the similar components of the tab shaver assembly 102 are referenced by primed reference numerals and are not individually described in detail again.

Now referring to FIG. 18, the male die 190 of the tab shaver assembly 102 comprises a generally cylindrical configuration with an increased diameter step 196 that functions to locate the male die 190 in the blind hole 142' in the boss 106B' of the base support 106' (see FIG. 16). The upper end 126' is machined to a spherical configuration having a radius substantially equal to the spherical radius of the donor material 14. A plurality of arms 198 extend longitudinally from the outer circumferential surface of the male die 190. Arms 198 are preferably spaced equidistantly and each include a width substantially equal to the distance between the tabs 24 of the die-cut donor material 14. In this manner, when the die cut donor material 14 is removed from the outline cutter assembly 100 of the invention, it can be seated upon the upper end 126' of the male die 190 with the tabs 24 thereof extending radially outwardly between the respective arms 198. The donor material 14 may be secured into position by means of the vacuum hole 144', blind holes 142' and 104B', suction holes 104S, and a vacuum source such as the spring-loaded medical syringe 146'.

The female die 192 is positioned within, or formed integrally with (as shown), the central bore 150' of the hand support 110'. As best shown in FIGS. 16 and 17, the female die 192 simply comprises a central hole 200 that has a diameter appreciably greater than the diameter of the male die 190. The female die 192 is positioned vertically within the central bore 150' of the hand support 110' such that the central hole 200 bends over the tabs 24 of the donor material 14 along the length of the male die 190 as the hand support 110 is seated onto the upper surface 106S' of the base support 106'. Most preferably, the diameter of central hole 200 is marginally greater than the diameter of the male die 190 (equal to the diameter of the central extent 16) plus twice the thickness of the Bowman's membrane 28 (e.g. 2×100 microns). Being marginally greater in diameter than the combined width of the central extent 16 and two layers of Bowman's membrane 28, it can be appreciated that tabs 24 would be forced to bend over the upper end 126' of the male die 190 and lay down along the length of the male die 190 as the central hole 200 of the female die 192 is moved downwardly into its seated position.

The tab shaver punch 194 is similar in design to the tab incisor punch 112 described above. Consequently, primed reference numerals are used in the drawings to refer to the similar components of the tab shaver punch 194 and are not discussed separately.

The annular cutter 182' of the tab shaver punch 194 includes an extended length (greater than that of the annular cutter 182 of the tab incisor punch 112). Furthermore, the diameter of the lumen of the annular cutter 182' is slightly enlarged to be substantially equal to the diameter of the central extent 16 plus twice the thickness of the Bowman's membrane 28 (e.g. 2×100 microns). With the increased diameter and increased length of the annular cutter 182', it should be appreciated that as the tab shaver punch 194 is inserted into the central bore 150' of the hand support 110' and is moved downwardly, the annular cutter 182' simply shaves off the excess donor material from the tabs 24 while leaving the Bowman's membrane 28 of the tabs 24 intact with the Bowman's membrane 28 of the central extent 16. Once the excess material is shaved off, the hand support 110' together with the tab shaver punch 194 may be removed from the base support 106'. When the vacuum is released, the die-cut, and shaved, donor material 14 may be removed from the male die 190, and is ready for transplantation according to the surgical method of the invention described above.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and methods and the combination and arrangement of parts and method steps may be resorted to without departing from the spirit and scope of the invention.

Now that the invention has been described,
What is claimed is:

1. A method of repairing a cornea of an eye, comprising the steps of:
providing a donor material of living tissue in the shape of a partial sphere, the donor material having an exterior Bowman's membrane of living tissue;
die cutting the donor material to define an outline configuration including a central extent and a plurality of tabs extending outwardly therefrom;
shaving the tabs to remove substantially all of the donor material therefrom leaving substantially only the Bowman's membrane such that the shaved tabs comprise substantially only Bowman's membrane, the Bowman's membrane of the shaven tabs being intact with the Bowman's membrane of the central extent;
forming a central aperture in the cornea to be repaired, the central aperture having a size and shape essentially that of the central extent of the donor material;
incising a plurality of pockets from the central aperture extending substantially laterally outwardly into the cornea, the pockets being positioned and sized and shaped to receive the respective shaven tabs when the central extent is positioned within the central aperture; and
positioning the central extent within the central aperture and imbricating the shaven tabs into the respective pockets.

2. The method as set forth in claim 1, wherein the step of die cutting the donor material comprises the step of positioning the donor material between male and female dies, the dies including the outline configuration such that the donor material is die-cut to the outline configuration as the male and female dies are mated.

3. The method as set forth in claim 2 further including the step of vertically supporting one of the dies allowing the donor material to be seated thereon prior to being die cut by the mating of the dies.

4. The method as set forth in claim 3, wherein the step of vertically supporting one of the dies comprises the step of vertically supporting the male die and wherein the female die is aligned and moved vertically downwardly toward the male die during mating thereby die cutting the donor material seated thereon into the outline configuration.

5. The method as set forth in claim 4, wherein the step of vertically moving the female die downwardly toward the male die comprises the step of coupling the female die with the male die by means of at least one guide pin.

6. The method as set forth in claim 5, further comprises the step of incising the central extent to the exterior Bowman's membrane thereof thereby leaving intact the exterior Bowman membrane of the central extent and the tabs.

7. The method as set forth in claim 6, wherein the step of incising the central extent comprises the step of aligning an annular cutter above the male die having the donor material seated thereon and then moving the annular cutter downwardly toward the male die to a depth no deeper than the height of the Bowman's membrane of the donor material seated on the male die.

8. The method as set forth in claim 7, further comprising the step of positioning an annular supporter about the male die for providing additional support to the donor material when seated thereon.

9. The method as set forth in claim 8, wherein the step of positioning the supporter about the male die comprises positioning an elastomeric ring about the male die to support the supporter rested thereon.

10. The method as set forth in claim 1, wherein the method of shaving the donor material from the exterior Bowman's membrane of the tabs comprises the steps of:
positioning the die-cut donor material between a male die and a female die, the dies being respectively configured to fold the tabs along the length of the male die when the dies are mated;
mating the dies to fold the tabs along the length of the male die; and
longitudinally shaving the donor material from the Bowman's membrane of the tabs.

11. The method as set forth in claim 10 further including the step of vertically supporting one of the dies allowing the donor material to be seated thereon prior to the tabs being shaved by the mating of the dies.

12. The method as set forth in claim 11, wherein the step of vertically supporting one of the dies comprises the step of vertically supporting the male die and wherein the female die is aligned and moved vertically downwardly toward the male die during mating thereby folding the tabs of the donor material seated thereon along the sides of the male die.

13. The method as set forth in claim 12, wherein the step of vertically moving the female die downwardly toward the male die comprises the step of coupling the female die with the male die by means of at least one guide pin.

14. The method as set forth in claim 13, wherein the step of shaving the donor material from the exterior Bowman's membrane of the tabs comprises the step of aligning an annular cutter above the male die having the donor material seated thereon and then moving the annular cutter downwardly between the mated dies to shave the donor material from the Bowman's membrane of the tabs folded along the side of the male die.

* * * * *